US00PP19490P2

(12) United States Plant Patent
Zary

(10) Patent No.: US PP19,490 P2
(45) Date of Patent: Nov. 25, 2008

(54) GRANDIFLORA ROSE PLANT NAMED 'JACCOLAP'

(50) Latin Name: *Rosa hybrida*
Varietal Denomination: JAColap

(75) Inventor: Keith W. Zary, Thousand Oaks, CA (US)

(73) Assignee: Jackson & Perkins Wholesale, Inc., Hodges, SC (US)

( * ) Notice: Subject to any disclaimer, the term of this patent is extended or adjusted under 35 U.S.C. 154(b) by 0 days.

(21) Appl. No.: 11/998,303

(22) Filed: Nov. 28, 2007

(51) Int. Cl.
*A01H 5/00* (2006.01)

(52) U.S. Cl. ..... Plt./136

(58) Field of Classification Search ..... Plt./136
See application file for complete search history.

*Primary Examiner*—Kent L. Bell
*Assistant Examiner*—Georgia Helmer
(74) *Attorney, Agent, or Firm*—Klarquist Sparkman, LLP

(57) ABSTRACT

Grandiflora rose plant having large 11–12 cm open blooms; apricot colored flowers with darker petal reverse; long cutting stems; and excellent ability to root and grow vigorously from softwood cuttings.

1 Drawing Sheet

Genus and Species: *Rosa hybrida.*
Variety Denomination: 'JACcolap'.

Origin of the Invention

The present invention relates to a new and distinct variety of a grandiflora rose plant named 'JACcolap' which was originated by me by crossing the variety 'JACmag' (U.S. Plant Pat. No. 3,998, seed parent), with an unnamed red hybrid (not patented, pollen parent). The pollen parent is a cross, unnamed seedling×unnamed seedling.

Background of the Invention

The primary objective of this breeding was to produce a new grandiflora rose variety having the flower size of the female (seed) parent combined with the long cutting stems and great own root vigor of the unnamed male (pollen) parent.

Brief Summary of the Invention

The objective was substantially achieved, along with other desirable improvements, as evidenced by the following unique combination of characteristics that are outstanding in the new variety and that distinguish if from its parents, as well as from all other varieties of which I am aware:

1. Large, 11–12 cm open blooms.
2. Apricot flowers with darker petal reverse.
3. Long cutting stems.
4. Excellent ability to root and grow vigorously from softwood cuttings.

Asexual reproduction of this new variety by cuttings, as performed at Somis, Calif., shows that the foregoing characteristics and distinctions come true to form and are established and transmitted through succeeding propagations.

Comparison with Parents

'JACcolap' differs from 'JACmag' in flower color ('JACcolap' has much deeper colored petal reverse), in petal count (typically 30 for 'JACmag' versus typically 35–40 for 'JACcolap'). 'JACcolap' differs from the male in flower color (red in the male parent) and petal count (typically 30 in the male parent versus typically, 35–40 in 'JACcolap').

Comparison with Similar Variety

The closest variety in flower shape and coloration is believed to be 'JACient' (U.S. Plant Pat. No. 6,725). 'JACient' has a different flower color (pink for 'JACient' versus apricot for 'JACcolap').

Brief Description of the Illustration

The accompanying illustration shows typical specimens of the vegetative growth and flowers of this new variety in different stages of development, depicted in color as nearly true as it is reasonably possible to make the same in a color illustration of this character.

Detailed Botanical Description

The following is a detailed description of my new rose cultivar with color descriptions using terminology in accordance with The Royal Horticultural Society (London) Colour Chart© 2001, except where ordinary dictionary significance of color is indicated.

Parentage:
*Seed parent.*—'JACmag' (U.S. Plant Pat. No. 3,998).
*Pollen parent.*—Unnamed hybrid (not patented); The parentage of the pollen parent is unnamed seedling× unnamed seedling.

FLOWER

Observations made from January 2006 to October 2007 from plants growing in a garden environment at Somis, Calif. The descriptions below are from plants that were four years old at the completion of the observations.

Blooming habit: Continuous.
Bud:
*Size.*—About 35 mm long and 30 mm in diameter when the petals start to unfurl.
*Form.*—The bud form is long, pointed ovoid.

*Color.*—When sepals first divide, bud color is Orange-Red Group 34A. When half blow, the upper sides of the petals are Yellow-Orange Group 22B on about the lower one-half of the petals. The color is Red Group 36B on about the outer one-half of the petals. The lower sides of the petals are Orange-Red Group 35A on about the lower two-thirds of the petal, Red Group 48C on about the outer one-third of the petal.

*Sepals.*—Color: Upper surface: Green Group 138B. Lower surface: Yellow-Green Group 146A. Length: 15–17 mm. Width: 11–12 mm. Shape: Subulate. Surface: Hoary. There are three lightly appendaged sepals. There are two unappendaged sepals with hairy edges.

*Receptacle.*—Color: Yellow-Green Group 146A. Shape: Funnel. Size: Large, about 12 mm long×10 mm in width. Surface: Smooth.

*Peduncle.*—Length: Short, averaging about 45 mm. Surface: Rough, prickly. 10–15 prickles every 10 mm of peduncle. Prickles average 2 mm long and are Green-White Group 157A in color. Color: Yellow-Green Group 146A. Strength: Stiff, heavy.

Bloom:

*Size.*—Large. Average open diameter is about 11–12 cm.

*Borne.*—Singly, several together in clusters of 3–5 blooms having flat shape.

*Stems.*—Strength: Strong. Average length is about 40–50 cm with a diameter of 7–8 mm.

*Form.*—When first open: High centered. Permanence: Petals curl with age.

*Petalage.*—Number of petals under normal conditions: 35–40.

*Color.*—The upper sides of the petals are Yellow-Orange Group 22B on about the outer one-half of the petal and Red Group 36B on about the inner one-half of the petal. The reverse sides of the petals are Orange-Red Group 35A on about the lower two-thirds of the petal and Red Group 48C on about the outer one-third of the petal. The base of the petals has a distinct color spot, about 5 mm×5 mm of Yellow Group 12B. The major color on the upper sides is Red Group 36B.

Variegations.—None.

*Discoloration.*—The general tonality at the end of the first day: No change. At the end of the third day: Fading toward Red Group 55B. Further aging: Fades to Red Group 55C by day 5 or 6.

*Fragrance.*—Moderate, sweet tea rose scent.

Petals:

*Thickness.*—Thick.

*Surface texture.*—Smooth.

*Shape.*—Obovate.

*Margin.*—Entire.

*Apex shape.*—Obtuse to rounded.

*Base shape.*—Rounded.

*Form.*—Tips slightly recurved.

*Arrangement.*—Imbricated.

*Petaloids.*—Number: Varies from 3 to 7. Size: 8–30 mm in length and 3–15 mm wide. Color like the petals.

*Persistence.*—Petals drop off cleanly before drying.

*Lastingness.*—On the plant: Long (about 5–7 days). As a cut flower: Long (about 8–10 days).

Reproductive parts:

*Stamens.*—Number: 50–60. Length: 12 mm. Anthers: Length: 4 mm. Color: Yellow-Orange Group 22D. Filaments: Color: Orange-Red Group 33B. Length: 8 mm. Pollen: Color: Group 26B.

*Pistils.*—Number 70–80. Length: 6 mm. Styles: Color: Red Group 46A. Length: 4 mm. Stigmas: Color: Red Group 45D. Length: 1 mm.

*Hips.*—None observed.

PLANT

*Form.*—Bush.

*Growth.*—Vigorous, upright, branching.

*Age to maturity.*—Two years.

*Mature plant.*—Height: 5 feet (150 cm). Width: 4 feet (120 cm).

*Rootstock.*—On own root.

Foliage: Number of leaflets on normal mid-stem leaves: 5.

*Size.*—Large. About 120 mm long×100 mm wide.

*Quantity.*—Normal.

*Color.*—New foliage: Upper side: Green Group 137A. Lower side: Yellow-Green Group 147B with a blush on the leaflet edges of Greyed-Red Group 178B. Old foliage: Upper side: Green Group 139A. Lower side: Green Group 138A.

Leaflets:

*Size.*—About 45 mm long×30 mm wide.

*Shape.*—Pointed oval.

*Base shape.*—Rounded.

*Apex shape.*—Acuminate.

*Texture.*—Leathery.

*Edge.*—Serrated.

*Serrations.*—Single.

*Petiole.*—Color: Green Group 138B.

*Petiole rachis.*—Color: Yellow-Green Group 146B. Underside: Rough with prickles.

*Auricles.*—None observed.

*Stipules.*—Length: 15 mm, serrated.

*Disease resistance.*—Resistant to rust and mildew, susceptible to blackspot under normal growing conditions.

*Pest resistance.*—None observed.

*Vein color.*—Green Group 139B.

*Venation pattern.*—Reticulate.

Wood:

*New wood.*—Color: Yellow-Green Group 146A. Bark: Smooth.

*Old wood.*—Color: Green Group 138A. Bark: Smooth.

Prickles:

*Quantity.*—Ordinary on main canes from base; 6–8 per 15 cm of wood. Ordinary on laterals from main canes; 6–8 per 15 cm of wood.

*Form.*—Hooked downward.

*Length.*—6–8 mm.

*Color when young.*—Greyed-Purple Group 183D.

*Color when mature.*—Greyed-Yellow Group 161B.

Small prickles:

*Quantity.*—On main stalks: None observed. On laterals: None observed.

Winter Hardiness: Hardy to Zone 5.

I claim:

1. A new and distinct variety of grandiflora rose plant, substantially as herein shown and described, characterized particularly by large, 11–12 cm open blooms; apricot colored flowers with darker petal reverse; long cutting stems; and excellent ability to root and grow vigorously from softwood cuttings.

* * * * *

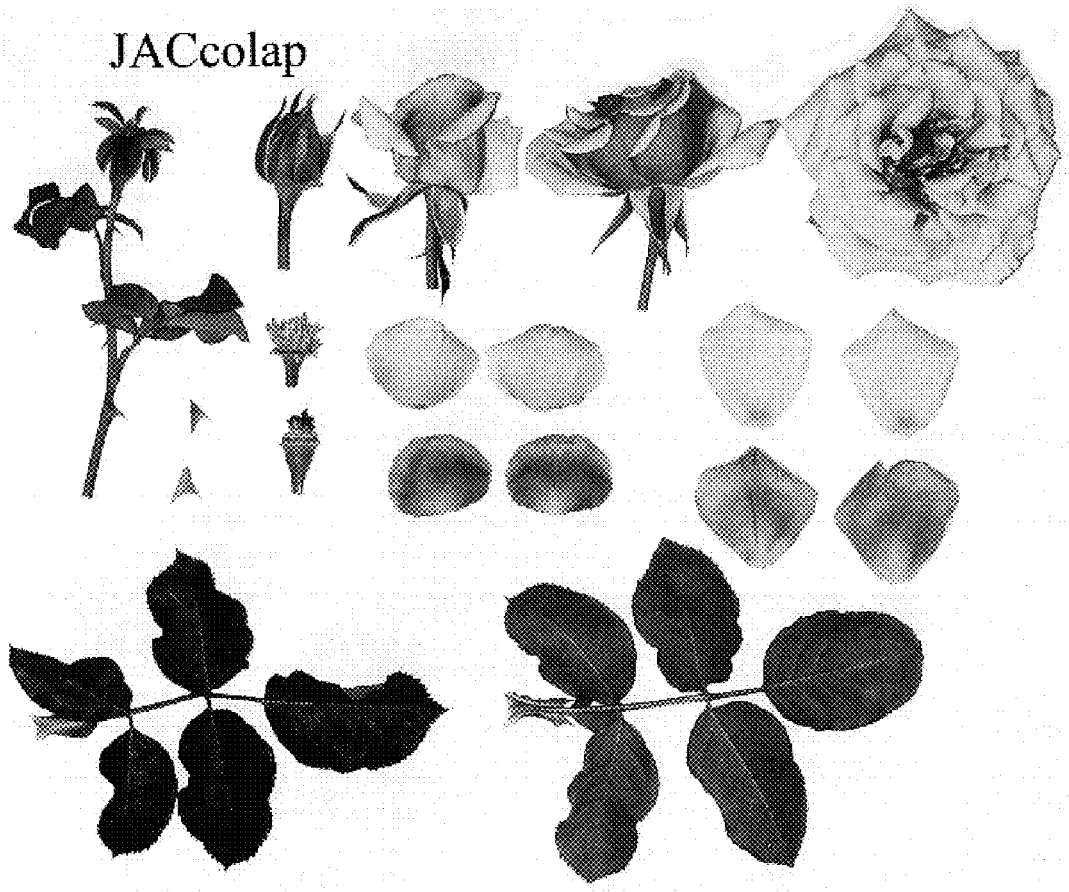
JACcolap